United States Patent
Wang et al.

(10) Patent No.: US 9,506,861 B2
(45) Date of Patent: Nov. 29, 2016

(54) METHOD FOR OBTAINING BINDING KINETIC RATE CONSTANTS USING FIBER OPTIC PARTICLE PLASMON RESONANCE (FOPPR) SENSOR

(71) Applicant: NATIONAL CHUNG CHENG UNIVERSITY, Min-Hsiung, Chia-Yi (TW)

(72) Inventors: Shau-Chun Wang, Chiayi (TW); Lai-Kwan Chau, Chiayi (TW); Ting-Chou Chang, Dounan Township, Yunlin County (TW); Chao-Ching Wu, Kaohsiung (TW)

(73) Assignee: NATIONAL CHUNG CHENG UNIVERSITY, Chia-Yi (TW)

( * ) Notice: Subject to any disclaimer, the term of this patent is extended or adjusted under 35 U.S.C. 154(b) by 126 days.

(21) Appl. No.: 14/063,763

(22) Filed: Oct. 25, 2013

(65) Prior Publication Data
US 2014/0051188 A1 Feb. 20, 2014

Related U.S. Application Data

(63) Continuation-in-part of application No. 13/470,984, filed on May 14, 2012, now abandoned.

(30) Foreign Application Priority Data

Nov. 14, 2011 (TW) .............................. 100141527 A
May 17, 2013 (TW) .............................. 102117666 A

(51) Int. Cl.
*G01N 21/552* (2014.01)
*G01N 21/55* (2014.01)
(Continued)

(52) U.S. Cl.
CPC ............ *G01N 21/55* (2013.01); *G01N 21/272* (2013.01); *G01N 21/554* (2013.01); *G01N 21/7703* (2013.01)

(58) Field of Classification Search
None
See application file for complete search history.

(56) References Cited

U.S. PATENT DOCUMENTS

2007/0109544 A1* 5/2007 Chau et al. .................... 356/445
2008/0227206 A1   9/2008 Karlsson et al.
(Continued)

OTHER PUBLICATIONS

Chiang et al., Fiber-optic particle plasmon resonance sensor for detection of interleukin-1 Beta in synovial fluids, Biosensors and Bioelectronics, 26, pp. 1036-1042, available online Aug. 20, 2010.*
(Continued)

*Primary Examiner* — Rebecca Martinez
(74) *Attorney, Agent, or Firm* — Muncy, Geissler, Olds & Lowe, P.C.

(57) ABSTRACT

A method for obtaining the binding kinetic rate constants using fiber optic particle plasmon resonance (FOPPR) sensor, suitable for a test solution with two or more concentrations, which employs the following major steps: providing one FOPPR sensor instrument system, obtaining optical time-resolved signal intensities starting at the initial time to the steady state of the two or more regions, substituting the measured signal intensity values into the formula which is derived by using the pseudo-first order rate equation model. In addition, this method measures the temporal signal intensity evolution under static conditions as the samples are quickly loaded. As a result, unlike the conventional device where the sample is continuously infused, the method is able to measure the association and dissociation rate constants of which the upper bounds are not limited by the sample flow rate.

9 Claims, 13 Drawing Sheets

(51) Int. Cl.
*G01N 21/27* (2006.01)
*G01N 21/77* (2006.01)

(56) References Cited

U.S. PATENT DOCUMENTS

2009/0066957 A1 3/2009 Shaw

2010/0182607 A1 7/2010 Chau et al.

OTHER PUBLICATIONS

Hsu et al., "Integration of fiber optic-particle plasmon resonance biosensor with microfluidic chip", Available online Apr. 22, 2011, Analytica Chimica Acta, 697, pp. 75-82.

* cited by examiner

METHOD FOR OBTAINING BINDING KINETIC RATE CONSTANTS USING FIBER OPTIC PARTICLE PLASMON RESONANCE (FOPPR) SENSOR

CROSS-REFERENCE TO RELATED APPLICATION

This is a continuation-in-part application of patent application Ser. No. 13/470,984 filed on May 14, 2012, which claims the priority benefit of Taiwan patent application serial no. 100141527, filed Nov. 14, 2011 and is now pending. This application also claims the priority benefits of Taiwan application serial no. 102117666, filed on May 17, 2013. The entirety of each of the above-mentioned patent applications is hereby incorporated by reference herein and made a part of this specification.

BACKGROUND OF THE INVENTION

1. Field of the Invention

The present invention relates to a method for obtaining binding kinetic rate constants using a fiber optic particle plasmon resonance (FOPPR) sensor, and particularly, a method for obtaining binding kinetic rate constants using a fiber optic particle plasmon resonance (FOPPR) sensor with simple and concise computation.

2. Description of the Related Art

Chemical thermodynamics practices the research of equilibrium characteristics of chemical reactions; it majorly focuses on the initial state and the final state of a chemical reaction. In contrast, chemical kinetics studies the reaction rate during a chemical reaction process. Chemical kinetics is frequently applied to the related research of the biological molecule association capability. The formation constant $K_f$, the association constant $k_a$, and the dissociation constant $k_d$ are all important parameters of chemical kinetics. For chemical kinetics of biological molecules, the association constant represents the formation rate of molecule complexes, wherein dissociation constant represents the stability of molecule complexes.

A biosensor is one type of device designed to detect analyte of biological molecules. Moreover, a biosensor is also equipped with the ability to monitor the variation of a chemical reaction and the function to convert the variation into specific signals for convenient observation. Thus, chemical kinetics studies can be conducted by observing related specific signals, for example, the data of recorded specific signals can be used to calculate the dissociation constant or the association constant of chemical kinetics.

However, the aforementioned biosensor needs to adopt a fluorescent mechanism to label a test analyte, this will alter the properties of the test analyte. Besides, the determination range of the association constant $k_a$ and the dissociation constant $k_d$ are confined to the test solution flow rate, due to the design of constantly infusing test solution in conventional plasmon resonance sensor (for example, the Biacore system). The above are the technical issues needs to be solved.

SUMMARY OF THE INVENTION

Based on the problems of the prior arts, the inventors, with many years of research development and plenty of practical experience, propose a method for obtaining binding kinetic rate constants using a fiber optic particle plasmon resonance (FOPPR) sensor to serve as the realization and basis to improve the above problems.

One of the objectives of the present invention is to provide a method for obtaining binding kinetic rate constants using a fiber optic particle plasmon resonance (FOPPR) sensor with simple and concise computation.

Another objective of the present invention is to provide a method for obtaining binding kinetic rate constants using a fiber optic particle plasmon resonance (FOPPR) sensor without using a fluorescent mechanism to mark a test analyte.

One further objective of the present invention is to provide a method for obtaining binding kinetic rate constants using a fiber optic particle plasmon resonance (FOPPR) sensor which can be used to estimate the kinetic parameters not influenced by flow rate of test analyte by merely acquiring the time-resolved light signal intensities in a static condition starting at the initial reaction time.

Based on the above objectives of the present invention, the present invention presents a method for obtaining binding kinetic rate constants using a fiber optic particle plasmon resonance (FOPPR) sensor, suitable for test solutions with at least two different concentrations, also suitable for test solutions with a plurality of concentrations. The operation steps are as follows:

provide a fiber optic particle plasmon resonance sensor, wherein the fiber optic particle plasmon resonance sensor at least comprises an isotropic light source to emit a light beam; a photoreceiver, for example, a photodiode; and a fiber sensor chip, wherein the fiber sensor chip is located between the light source and the photoreceiver and the fiber sensor chip comprises:

an optical fiber, wherein the optical fiber comprises a first region and a second region; the first region is located at two corresponding sides of the second region, wherein the first region comprises a fiber core, a cladding, and a protective layer, the refractive index of the fiber core is greater than that of the cladding such that the light beam can propagate within the fiber core; and the second region comprises the fiber core, the cladding, a noble metal nanoparticle layer, and a bio-recognition layer;

a first plate, wherein the first plate comprise a trench and the trench is used to place the fiber; and a second plate, wherein one side of the second plate is vertically installed a first tube and a second tube, the first tube is hollow and comprises a first opening, the second tube is hollow and comprises a second opening, the first tube and the second tube are connected to the second plate, the other side of the second plate which is opposite to the side installed the first tube and the second tube is face-to-face against the side of first plate containing the trench such that the fiber can be placed between the first plate and the second plate and into the trench within the first plate, and the second plate is placed face-to-face against the first plate to seal them off;

allow the light beam from the light source of the fiber optic particle plasmon resonance sensor to enter the fiber sensor chip and propagate within the fiber core due to total internal reflection, and let the photoreceiver of the fiber optic particle plasmon resonance sensor receive a light signal; quickly inject a reference solution into the first opening of the first tube, wherein the first opening is served as a flow inlet, such that the reference solution flows through the fiber sensor chip and remain in a static condition within the first tube; inject N test solutions sequentially into the first opening of the first tube, such that in sequence the test solutions flow through the fiber sensor chip and remain in a static condition within the trench of the first plate till the next injection, wherein each of the test solutions comprises a separate concentration $C_i$, where the integer i is from 1 to N, and the number of N is equal to or greater than 2;

the fiber optic particle plasmon resonance sensor converts the light signals received by the photoreceiver into a curve diagram of time-resolved light signal intensity, wherein the number of segments i in the curve of the curve diagram is the same as that of test solutions of concentration $C_i$, and each segment numbered as i is corresponding to the time-resolved light signal intensity generated by each of the injected test solutions of concentration $C_i$ in sequence, respectively;

obtain each of the time-resolved light signal profiles in a static condition starting at the initial time of the segments in the curve diagram $I_t$, the light signal intensity values of the segments at the steady states $I_{eq}$, and the reference light signal intensity $I_0$ corresponding to the average signal intensity level of the reference solution, respectively;

obtain the time-resolved light signal intensity values $I_t$ during the initial time span following that each of the test solutions is just filled up the trench and remains at a static condition, take $I_t$ into a fraction formula $[(I_t-I_{eq})/(I_0-I_{eq})]$ to calculate a plurality of fraction logarithm values of the fraction formula, $\ln[(I_t-I_{eq})/(I_0-I_{eq})]$, then subtracted by the value of $\ln[(I_0-I_{eqi})/(I_{eqi(i-1)}-I_{eqi})]$ to adjust the intercept of the linear formula as zero when the reference light signal intensity prior to the initial time is not obtained using the reference solution (i≥2), and execute a linear regression by using the logarithm values versus time to obtain a plurality of linear line diagrams corresponding to the number of the segments;

obtain a slope $S_i$ of each linear line in the linear line diagrams, respectively; and use the concentrations $C_i$ and the corresponding slopes S of different test solutions to execute another linear regression to yield a slope and an intercept of each regression line $S(C_i)=k_a C_i + k_d$. The values of slope and intercept are an association constant $k_a$ and a dissociation constant $k_d$, respectively.

The method for obtaining binding kinetic rate constants using a fiber optic particle plasmon resonance (FOPPR) sensor of the present invention utilize N different test solutions to obtain a curve diagram of time-resolved light signal intensity of the N concentrations in a static condition. N slopes can be obtained after a linear regression over the above curve diagram. After executing another linear regression over the N slopes versus the N concentrations, finally the $k_a$ value and the $k_d$ value can be obtained, wherein the N value is equal to or greater than 2.

The present invention does not need to use a fluorescence mechanism to label the test analyte, thus it will not alter the properties of the test analyte. Moreover, the present invention detects the time-resolved light signal intensity after the test solution is quickly injected and remains in a static condition. Unlike the conventional plasmon resonance sensor using a flow system (for example, the Biacore system), the upper bounds of the association constant $k_a$ and the dissociation constant $k_d$ estimated by the present invention will not be limited by the flow rate of the test solution.

To increase further understanding of the technical characteristics and the efficacy of the present invention, preferred embodiments and detailed explanations are provided below.

DETAILED DESCRIPTION OF THE PREFERRED EMBODIMENTS

With reference to the drawings, thereafter, the preferred embodiments of a method for obtaining binding kinetic rate constants using a fiber optic particle plasmon resonance (FOPPR) sensor in accordance with the present invention are illustrated. In order to be understood easily, the same components in the following embodiments are labeled as the same numeral.

Figure 1:
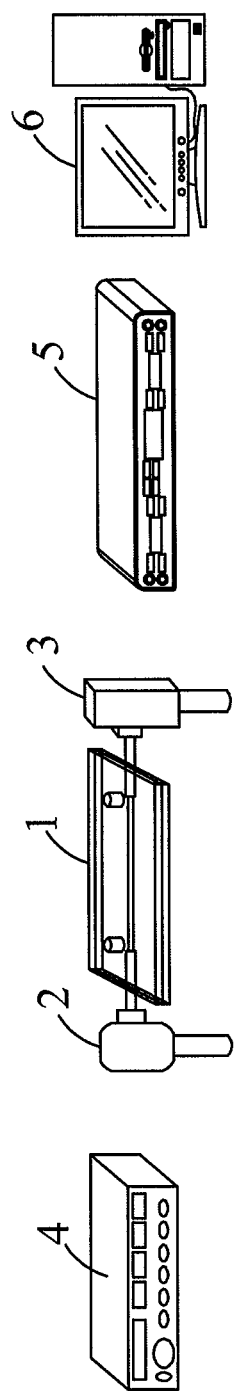
FIG. 1 is the three dimensional diagram showing a fiber optic particle plasmon resonance sensor of a method for obtaining binding kinetic rate constants using a fiber optic particle plasmon resonance (FOPPR) sensor according to the preferred embodiment of the present invention.

Referring to FIG. 1, FIG. 1 is the three dimensional diagram showing a fiber optic particle plasmon resonance sensor of a method for obtaining binding kinetic rate constants using a fiber optic particle plasmon resonance (FOPPR) sensor according to the preferred embodiment of the present invention. The fiber optic particle plasmon resonance sensor of the present invention at least comprises a fiber sensor chip 1, a light source 2, and a light receiving device 3. The fiber sensor chip 1 is located between the light source 2 and photoreceiver 3. The light source is a single frequency light, for example, a laser, or a narrow band light, for example, a light-emitting diode.

Referring to FIG. 1, FIG. 1 is the three dimensional diagram showing a fiber optic particle plasmon resonance sensor of a method for obtaining binding kinetic rate constants using a fiber optic particle plasmon resonance (FOPPR) sensor according to the preferred embodiment of the present invention. The fiber optic particle plasmon resonance sensor of the present invention optionally comprises a power supply unit 4, a signal processing unit 5, and a computer 6. The power supply unit can be any form of power supply apparatus, for example, a waveform generator, wherein the signal processing unit can be any form of signal processing apparatus, for example, a lock-in amplifier. The aforementioned power supply unit 4 is used to generate a functional driving signal of a fixed frequency square wave to the light source 2, wherein the power supply unit 4 also generates a reference signal to the signal processing unit 5. The aforementioned signal processing unit 5 receives the light sign coming from the photoreceiver 3 and correlates the light signal with the reference signal to generate a processed signal. The computer 6 receives the processed signal coming from the signal processing unit 5 to save as a data file and displays the data file for evaluation. The installation of the aforementioned power supply unit 4, the signal processing unit 5, and the computer 6 is to raise the signal-to-noise ratio (S/N ratio) of the light signal.

Figure 2:
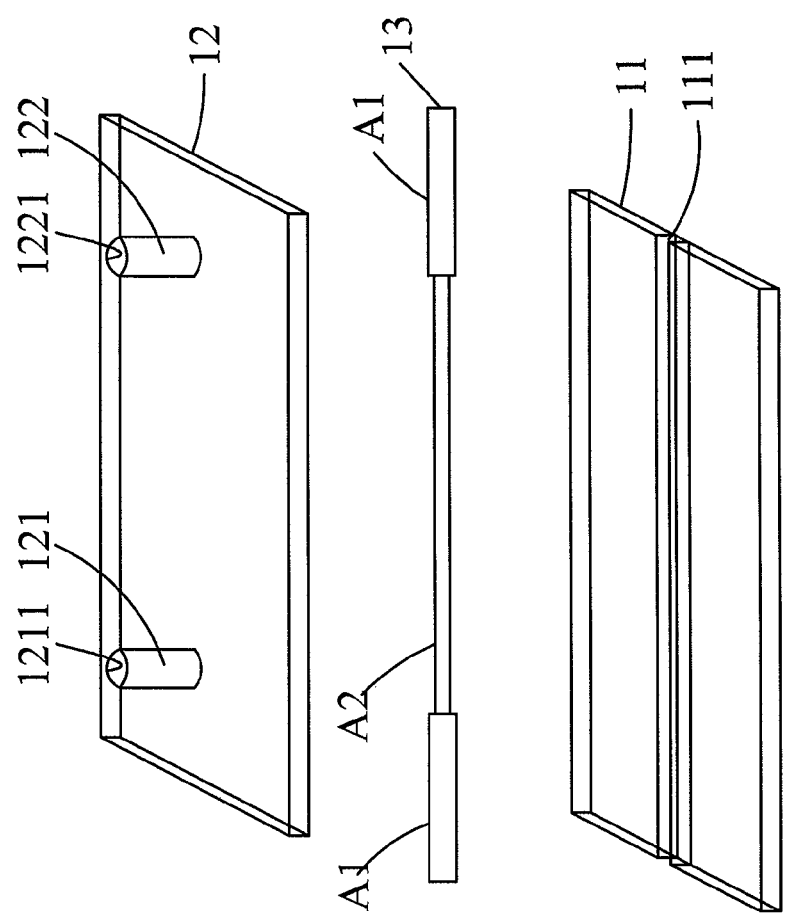
FIG. 2 is the three dimensional decomposition diagram showing a fiber sensor chip of a fiber optic particle plasmon resonance sensor according to the preferred embodiment of the present invention.

Referring to FIG. 2, FIG. 2 is the three dimensional decomposition diagram showing a fiber sensor chip of a fiber optic particle plasmon resonance sensor according to the preferred embodiment of the present invention. The fiber sensor chip of the present invention comprises a first plate 11, a second plate 12, and an optical fiber 13. The first plate 11 contains a trench 111 and the trench 111 is used to place the optical fiber 13. One side of the second plate 12 is vertically installed a first tube 121 and a second tube 122, the first tube 121 is hollow and comprises a first opening 1211, the second tube 122 is hollow and comprises a second opening 1221, the first tube 121 and the second tube 122 are connected to the second plate 12, the other side of the second plate 12 which is opposite to the first plate installed the first tube 121 and the second tube 122 is face-to-face against the side of first plate 11 containing the trench such that the optical fiber 13 can be placed between the first plate 11 and the second plate 12 and into the trench 111 within the first plate 11, and the second plate 12 is placed face-to-face against the first plate 11 to seal them off, such that the assembly of the fiber sensor chip 1 is finished [Referring to FIG. 1 for the assembled fiber sensor chip]. The aforementioned first plate or the second plate is made of plastic.

Figure 3A:
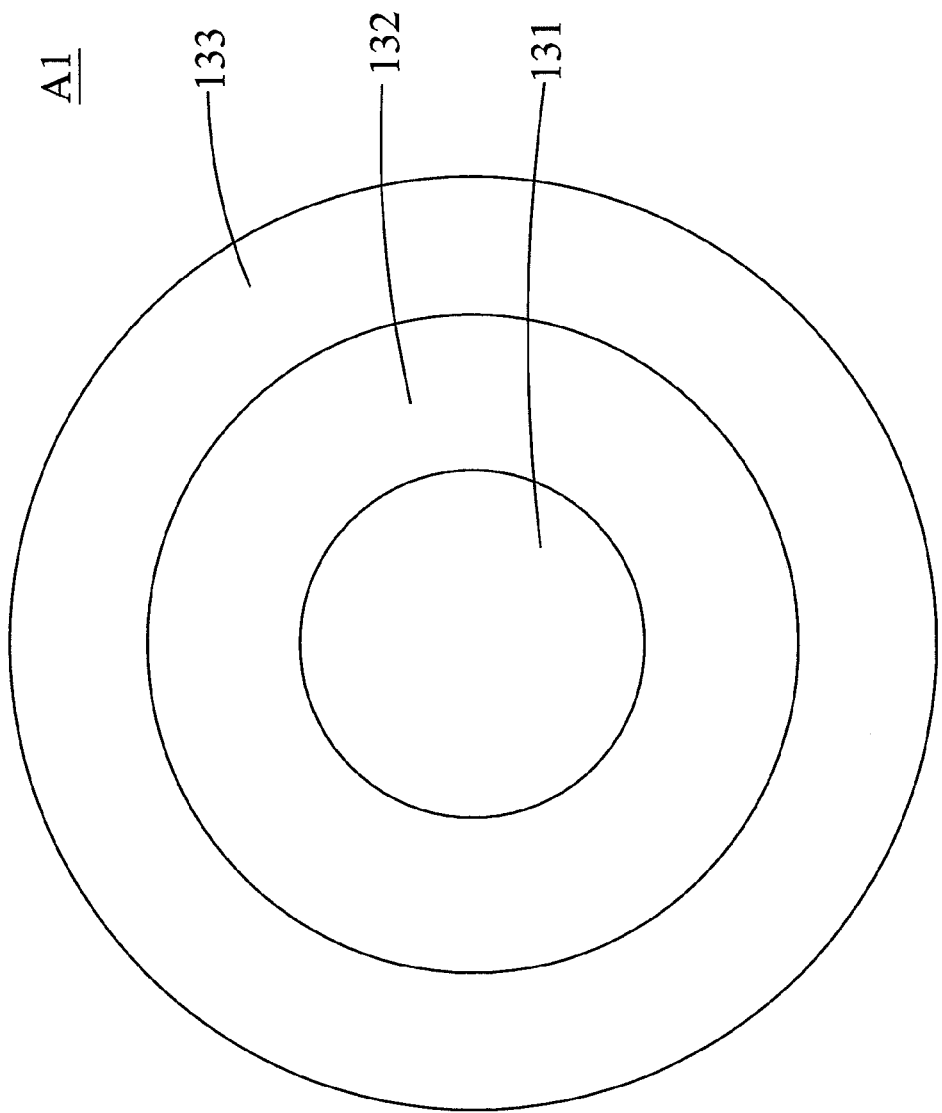
FIG. 3A is the cross section diagram showing the first region of a fiber sensor chip according to the preferred embodiment of the present invention.

Referring to FIG. 3A, FIG. 3A is the cross section diagram showing the first region of a fiber sensor chip according to the preferred embodiment of the present invention. The optical fiber 13 of the present invention comprises a first region A1 and a second region A2. The first region A1 is located at two corresponding sides of the second region A2, wherein the first region A1 comprises a fiber core 131, a cladding 132, and a protective layer 133. The aforementioned fiber core is made of silicon oxide and the cladding is made of polymeric material. A refractive index of the fiber core 131 is greater than that of the cladding 132 such that the light beam can propagate through the fiber core 131 due to total internal reflection.

Figure 3B:
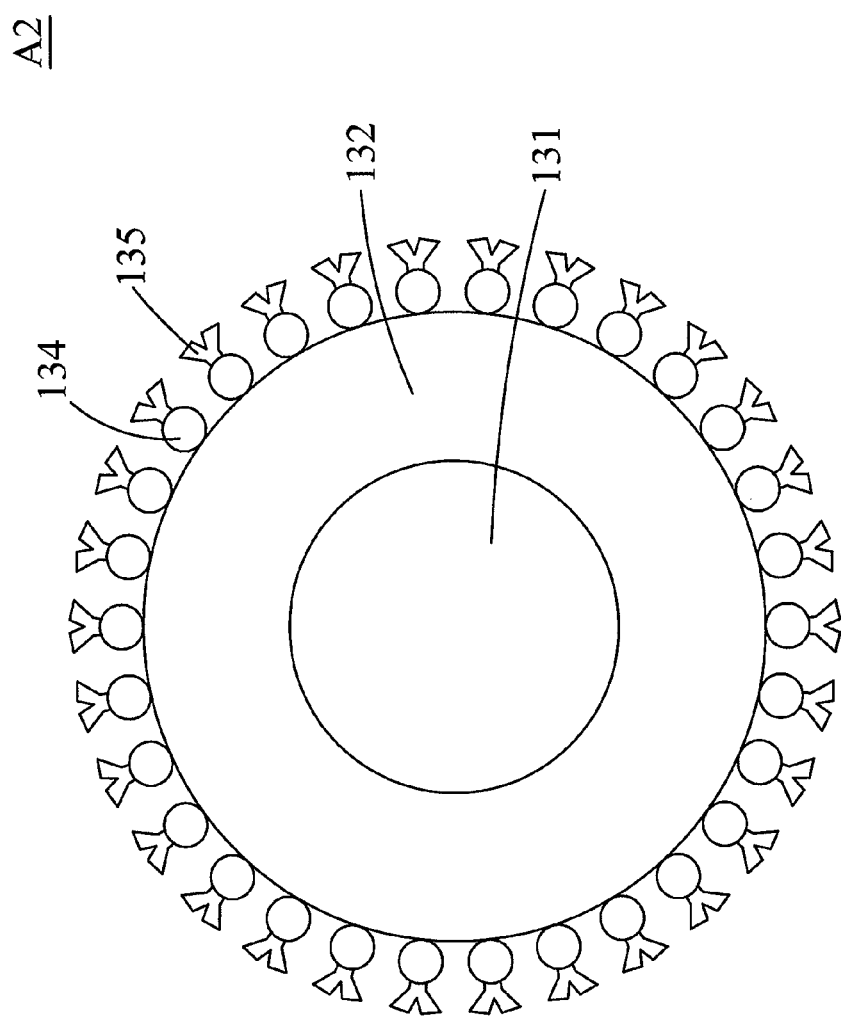
FIG. 3B is the cross section diagram showing the second region of a fiber sensor chip according to the preferred embodiment of the present invention.

Referring to FIG. 3B, FIG. 3B is the cross section diagram showing the second region of a fiber sensor chip according to the preferred embodiment of the present invention. The second region A2 of the fiber 13 of the present invention comprises the fiber core 131, the cladding 132, a noble metal nanoparticle layer 134, and a bio-recognition layer 135. The aforementioned fiber core 132 is made of silicon oxide and cladding 132 is made of polymeric material. The refractive index of the fiber core 131 is greater than that of the cladding 132. The noble metal nanoparticle layer 134 is made of nanogold or nanosilver. The noble metal nanoparticle layer 134 comprises a plurality of noble metal nanosphere, a plurality of noble metal nanorods, or a plurality of noble metal nanoshells. The surface of the noble metal nanoparticle layer 134 can be modified with various recognition units to generate the bio-recognition layer 135. The aforementioned bio-recognition layer 135 is an antibody, for example, an anti-mouse immunoglobulin (anti-mouse IgG), a lectin, a hormone receptor, a nucleic acid, or a carbohydrate. The aforementioned bio-recognition layer 135 is to detect an antigen, a cytokine, an antibody, a hormone, a growth factor, a neuropeptide, a hemoglobin, a plasma protein, a nucleic acid, a carbohydrate, a glycoprotein, a fatty acid, a phosphatidic acid, a sterol, an antibiotic, or a toxin. It is noteworthy to mention that the noble metal nanoparticle layer 134 and the bio-recognition layer 135 in FIG. 3B are magnified, not the practical scale, for the sake of easier understanding.

Figure 4A:
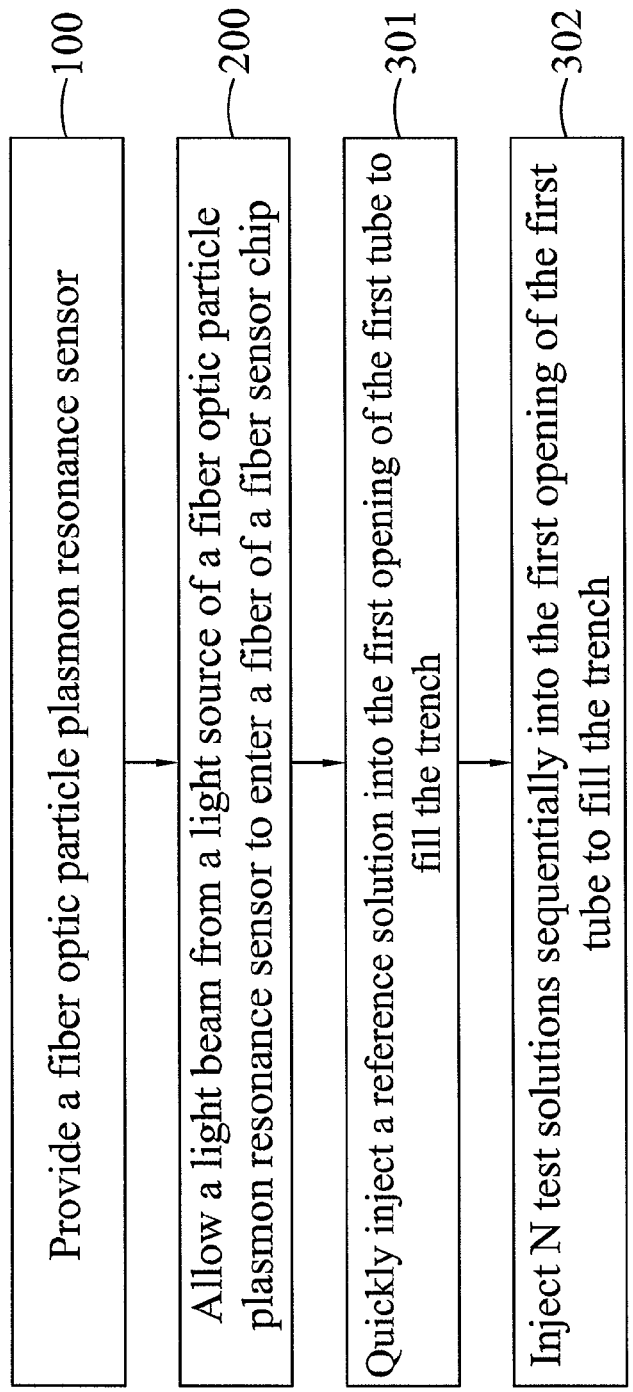
FIG. 4A is the first procedure diagram of a method for obtaining binding kinetic rate constants using a fiber optic particle plasmon resonance (FOPPR) sensor according to the preferred embodiment of the present invention.
Figure 4B:
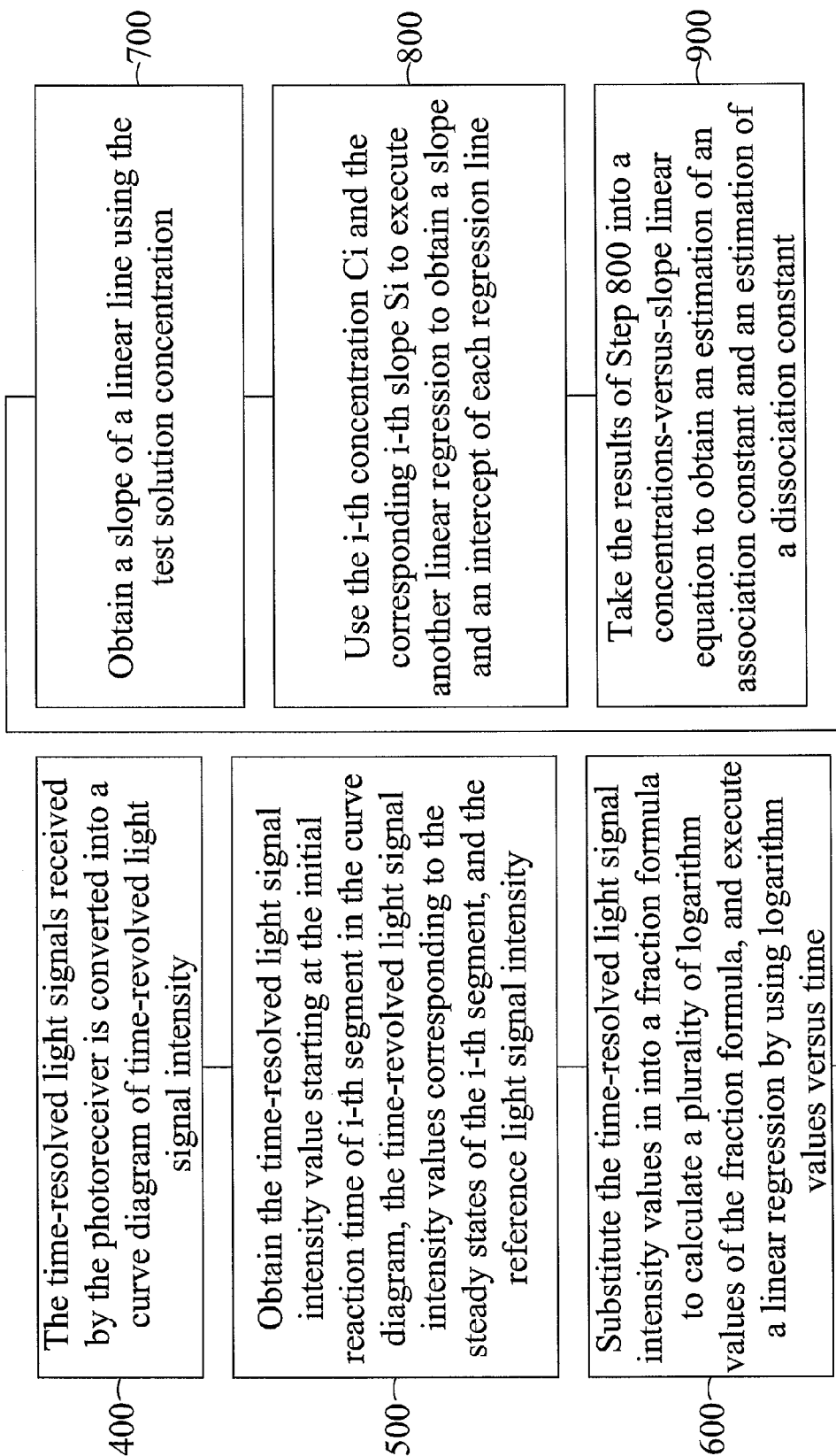
FIG. 4B is the second procedure diagram of a method for obtaining binding kinetic rate constants using a fiber optic particle plasmon resonance (FOPPR) sensor according to the preferred embodiment of the present invention.

Referring to FIGS. 4A and 4B, FIGS. 4A and 4B are the first and second procedure diagrams of a method for obtaining binding kinetic rate constants using a fiber optic particle plasmon resonance (FOPPR) sensor according to the preferred embodiment of the present invention. The kinetic constant estimation method of the present invention is suitable for N test solutions; the number N is equal to or greater than 2. In another word, the present invention can be applied to test solutions with at least two different concentrations, also suitable for test solutions with a plurality of concentrations.

Step 100: Provide the aforementioned fiber optic particle plasmon resonance sensor.

Step 200: Allow a light beam from a light source of a fiber optic particle plasmon resonance sensor 2 to enter a fiber 13 of a fiber sensor chip 1. The aforementioned light beam propagates within the fiber core 131 due to total internal reflection, and let the photoreceiver 3 of the fiber optic particle plasmon resonance sensor receive a light signal.

Step 301: Quickly inject a reference solution into the first opening 1211 of the first tube 121 to fill the trench 111, wherein the first opening 1211 is served as a flow inlet and the reference solution is, for example, deionized water or a buffer solution.

Step 302: Inject N test solutions sequentially into the first opening 1211 of the first tube 121, such that in sequence the test solutions quickly flow through the fiber sensor chip and remain in a static condition within the trench till the next injection, wherein each of the test solutions comprises a separate concentration $C_i$, where the integer i is from 1 to N, and the number of N is equal to or greater than 2; The following test solution concentration $C_{i+1}$ is greater than the preceding test solution concentration $C_i$.

Step 400: The time-resolved light signals received by the photoreceiver 3 is converted into a curve diagram of time-revolved light signal intensity. The number of segments in the curve of the curve diagram is the same as that of test solutions, and each segment is corresponding to the time-revolved light signal intensity generated by each of the injected test solutions in sequence, respectively. When N test solutions are used, the curve of the curve diagram comprises N segments, the i-th segment represents the time-revolved light signal intensity generated by the i-th test solution.

Step 500: Obtain the time-resolved light signal intensity value $I_i$ starting at the initial reaction time of the i-th segment in the curve diagram, the time-revolved light signal intensity values $I_{eqi}$ corresponding to the steady states of the i-th segment, and the reference light signal intensity $I_0$ corresponding to the average signal level of the reference solution, respectively. Refer to the subsequent FIG. 5 or FIG. 8 for the aforementioned cure diagram.

Step 600: Obtain the time-revolved light signal intensity values during the initial time span following that the test solution is just filled up the trench and remains at a static condition. Substitute the time-resolved light signal intensity values $I_t$ into a fraction formula $[(I_t-I_{eqi})/(I_0-I_{eqi})]$, to calculate a plurality of logarithm values of the fraction formula, which is derived based on a model under the assumption of a pseudo-first order reaction rate equation. The form of the final formula is a semi-logarithm linear formula of the fraction function of the time-revolved light signal intensity values. In addition, when the reference light signal intensity prior to the initial time is not obtained using the reference solution (i≥2), each logarithm value must be subtracted by the value of $\ln [(I_0-I_{eqi})/(I_{eq(i-1)}-I_{eqi})]$ to adjust the intercept of the linear formula as zero. A linear regression is executed by using the corrected logarithm values versus time to obtain a line diagram corresponding to one segment. Reference to the subsequent FIG. 6A for the aforementioned linear line diagram.

Step 700: Obtain a slope $S(C_i)$ of a linear line using the test solution concentration $C_i$.

Step 800: Use the i-th concentration $C_i$ and the corresponding i-th slope $S_i$ to execute another linear regression to obtain a slope and an intercept of each regression line.

Step 900: Take the results of Step 800 into a concentration-versus-slope linear equation $S(C_i)=k_aC_i+k_d$ to obtain estimations of an association constant and a dissociation constant.

The above steps can be applied to detect and analyze the same kind of test solutions with more than two different concentrations.

Figure 5:
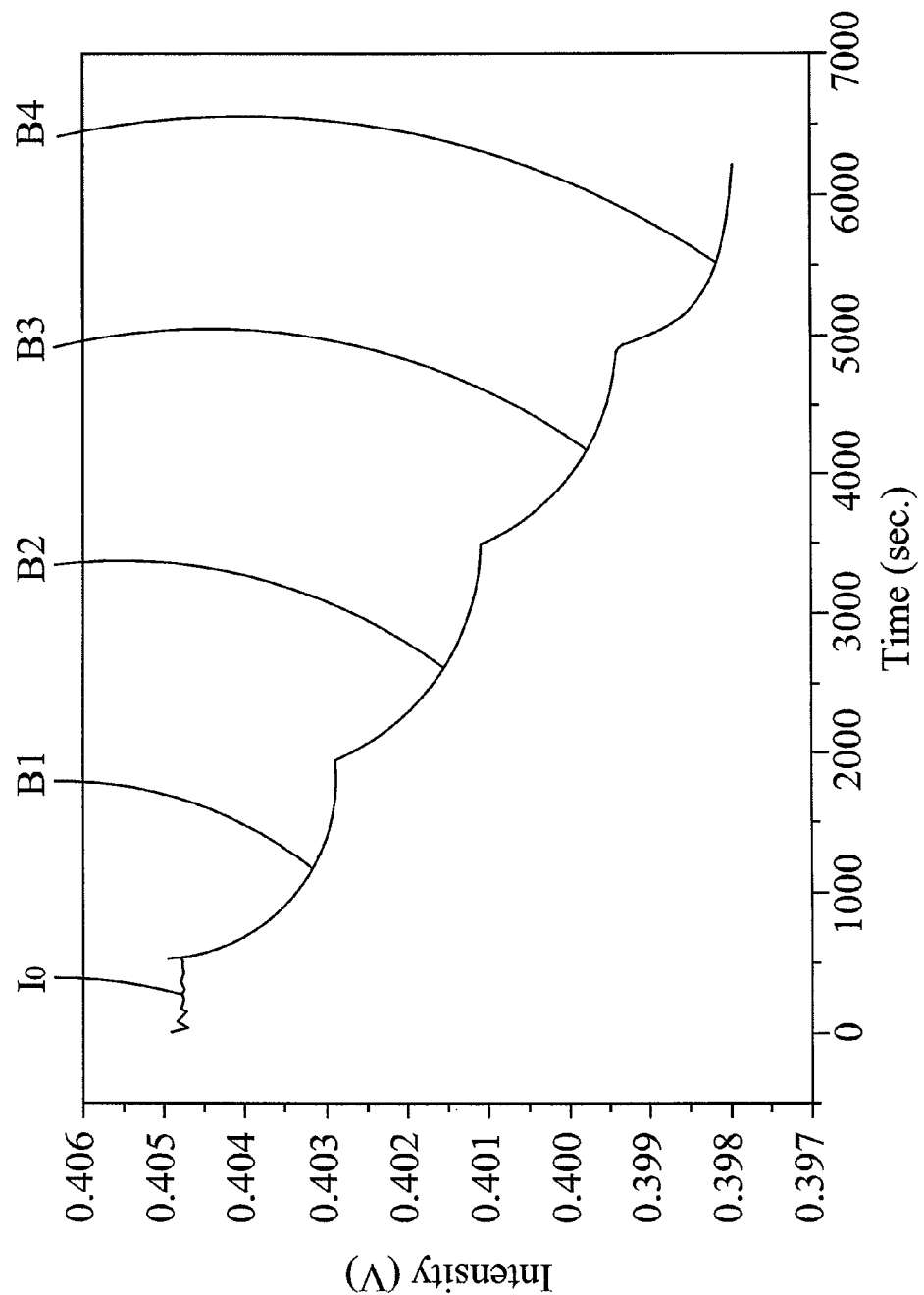
FIG. 5 is the curve diagram showing the use of ovalbumin (OVA) as a bio-recognition layer and anti-ovalbumin antibody (anti-OVA) as a test solution according to a kinetic constant estimation method according to the first embodiment of the present invention.

Referring to FIG. 5, FIG. 5 is the curve diagram showing the use of ovalbumin (OVA) as a bio-recognition layer and anti-ovalbumin antibody (anti-OVA) with four different concentrations as a test solution according to a kinetic constant estimation method described in the first embodiment of the present invention. The curve in the diagram comprises a first segment B1, a second segment B2, a third segment B3, and a fourth segment B4, wherein the third segment B3 and the fourth segment B4 represent the same test solution with two different concentrations. Obtain the time-revolved light signal intensity values $I_1$ and $I_2$ corresponding to the initial reaction time of the first and the second segments in the curve diagram, the light signal intensity values $I_{eq1}$ and $I_{eq2}$ corresponding to the steady states of the first and the second segments, and the reference light signal intensity $I_0$, respectively. The concentrations of the anti-ovalbumin antibody (anti-OVA) test solutions in the first segment B1, the second segment B2, the third segment B3, and the fourth segment B4 are 67 nM, 134 nM, 268 nM, and 536 nM.

Figure 6A:
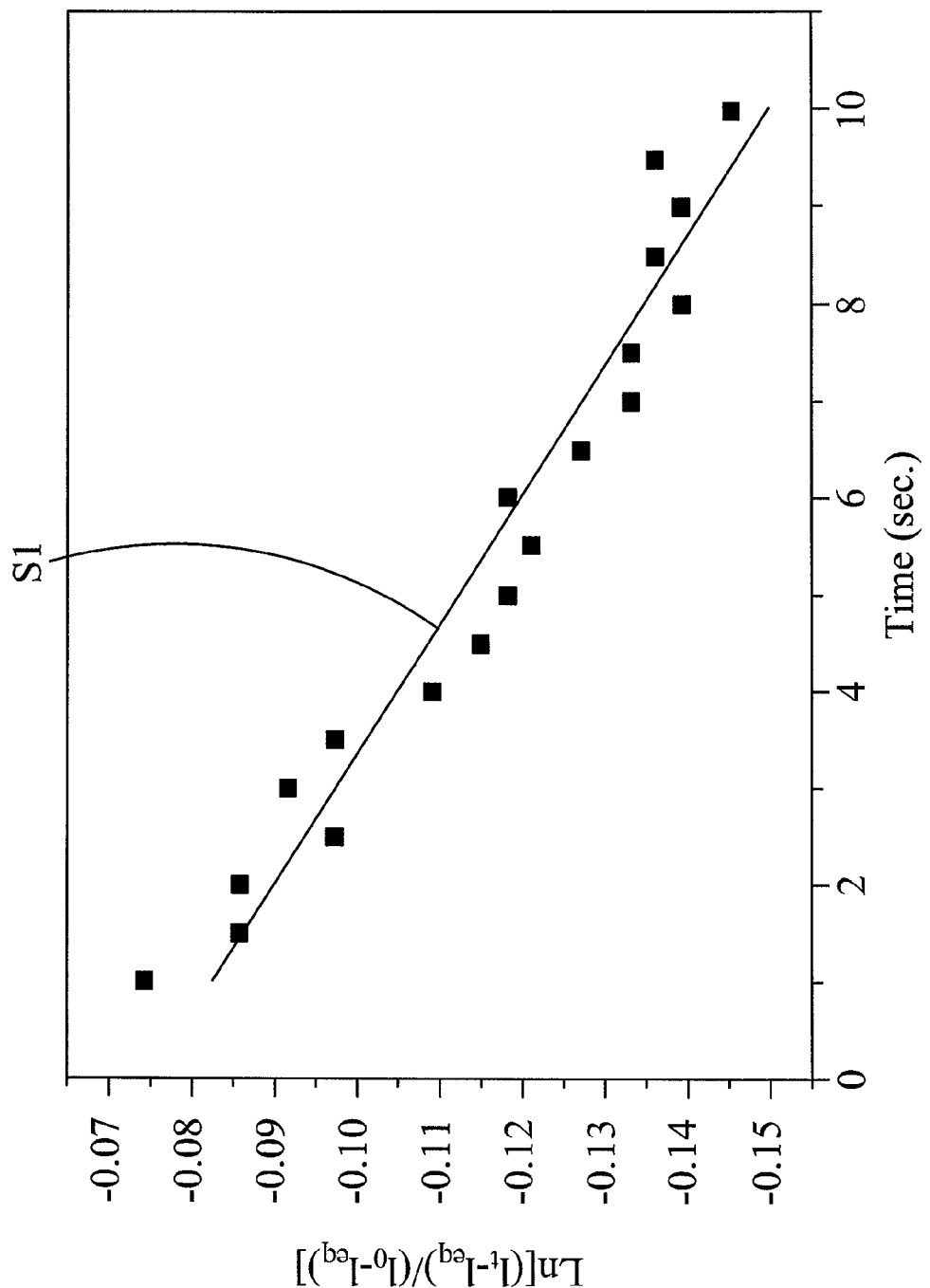
FIG. 6A is the first linear line diagram showing the use of ovalbumin (OVA) as a bio-recognition layer and anti-ovalbumin antibody (anti-OVA) as a test solution according to the kinetic constant estimation method of the present invention.
Figure 6B:
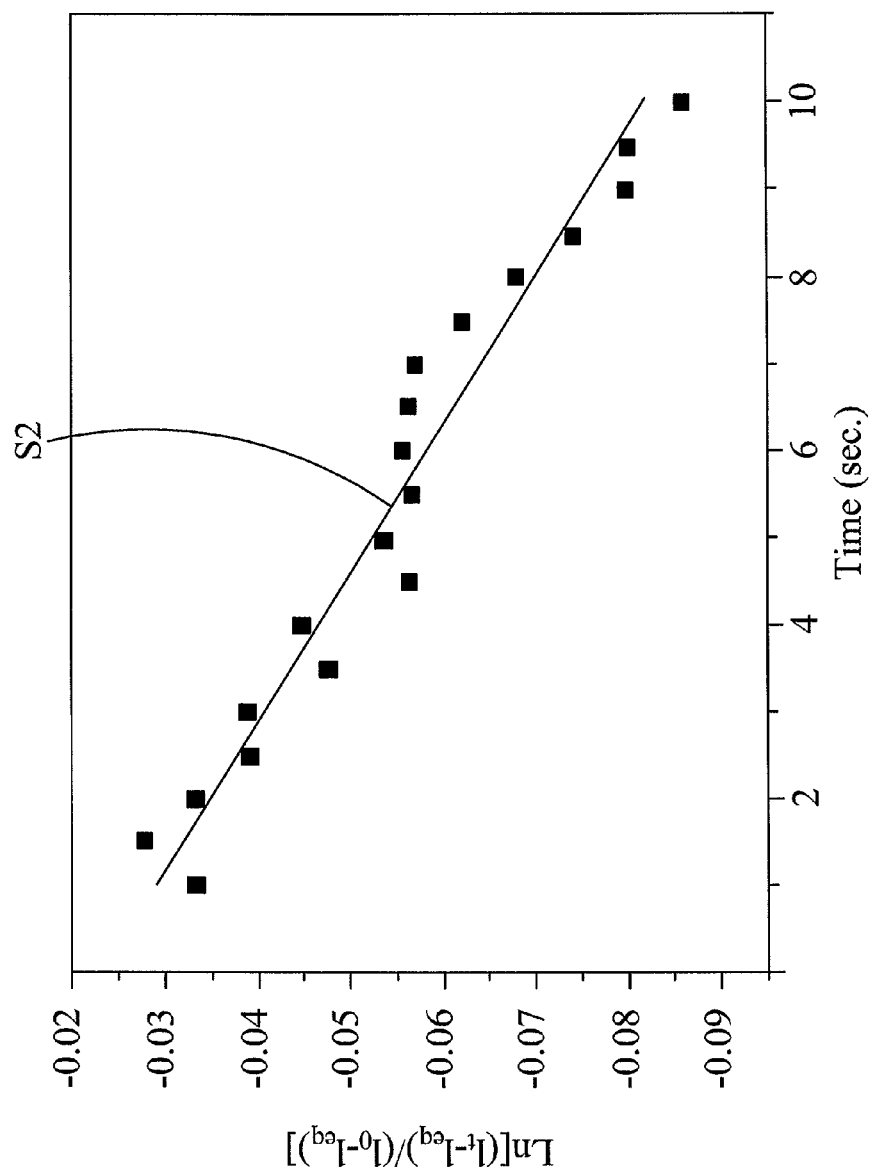
FIG. 6B is the second linear line diagram showing the use of ovalbumin (OVA) as a bio-recognition layer and anti-ovalbumin antibody (anti-OVA) as a test solution according to the kinetic constant estimation method of the present invention.

Referring to FIG. 6A and FIG. 6B, FIG. 6A and FIG. 6B are the first linear line and the second linear line diagrams showing the use of ovalbumin (OVA) as a bio-recognition layer and anti-ovalbumin antibody (anti-OVA) as a test solution according to the kinetic constant estimation method of the present invention. Take the time-revolved light signal intensity values into a formula $\ln [(I_t-I_{eq})/(I_0-I_{eq})]$ to calculate a plurality of fraction logarithm values, then execute a linear regression by using to the fraction logarithm values versus time to obtain a first line diagram corresponding to the first segment B1 and a second line diagram corresponding to the second segment B2. The concentrations of anti-ovalbumin antibody (anti-OVA) used in FIGS. 6A and 6B as the test solutions are 67 nM and 134 nM, respectively. The correlation coefficients of the data in of FIGS. 6A and 6B are both 0.97.

Figure 7A:
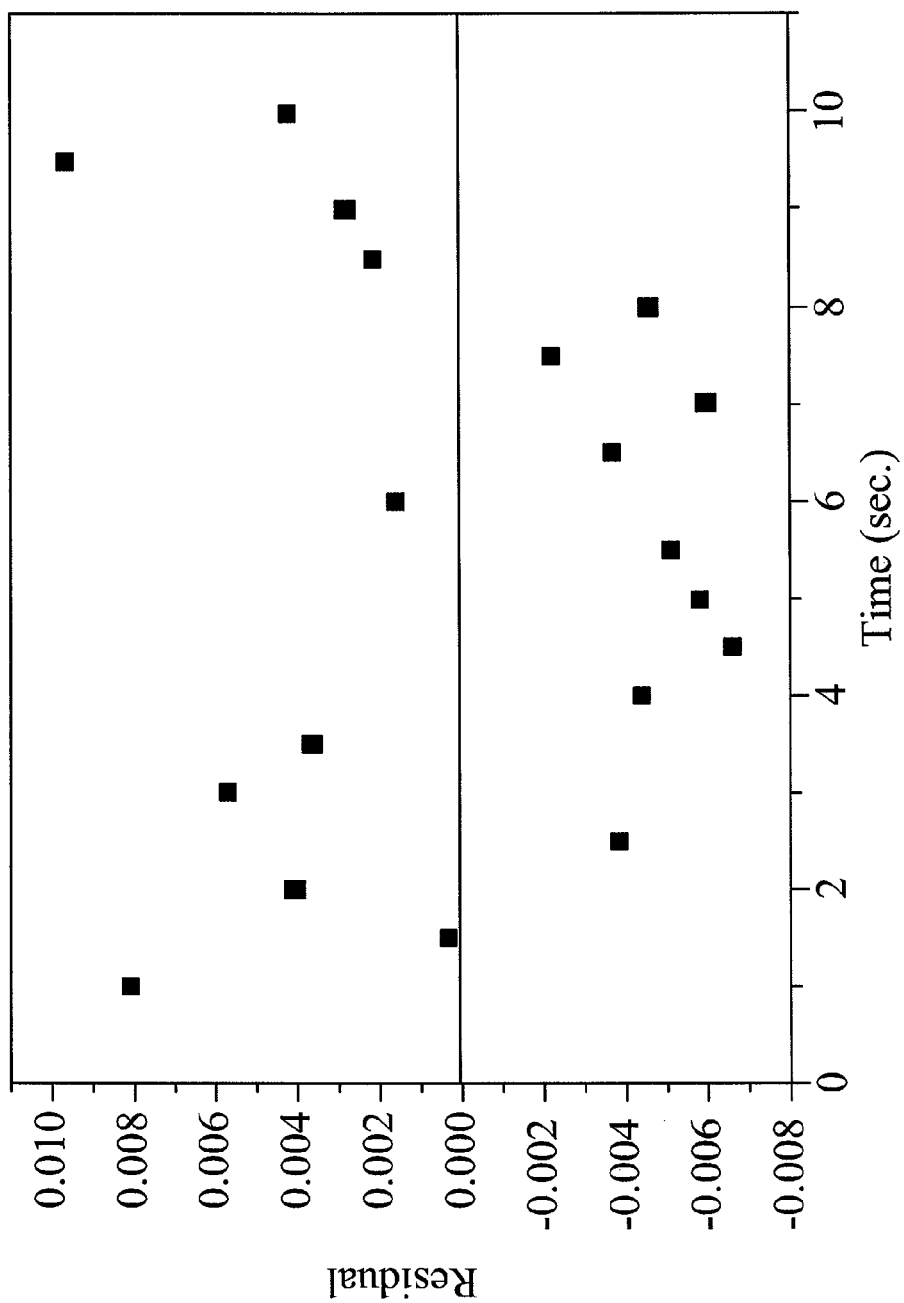
FIG. 7A is a diagram showing the residual analysis of the sample points and the linear regression line in FIG. 6A according to the first embodiment of the present invention.
Figure 7B:
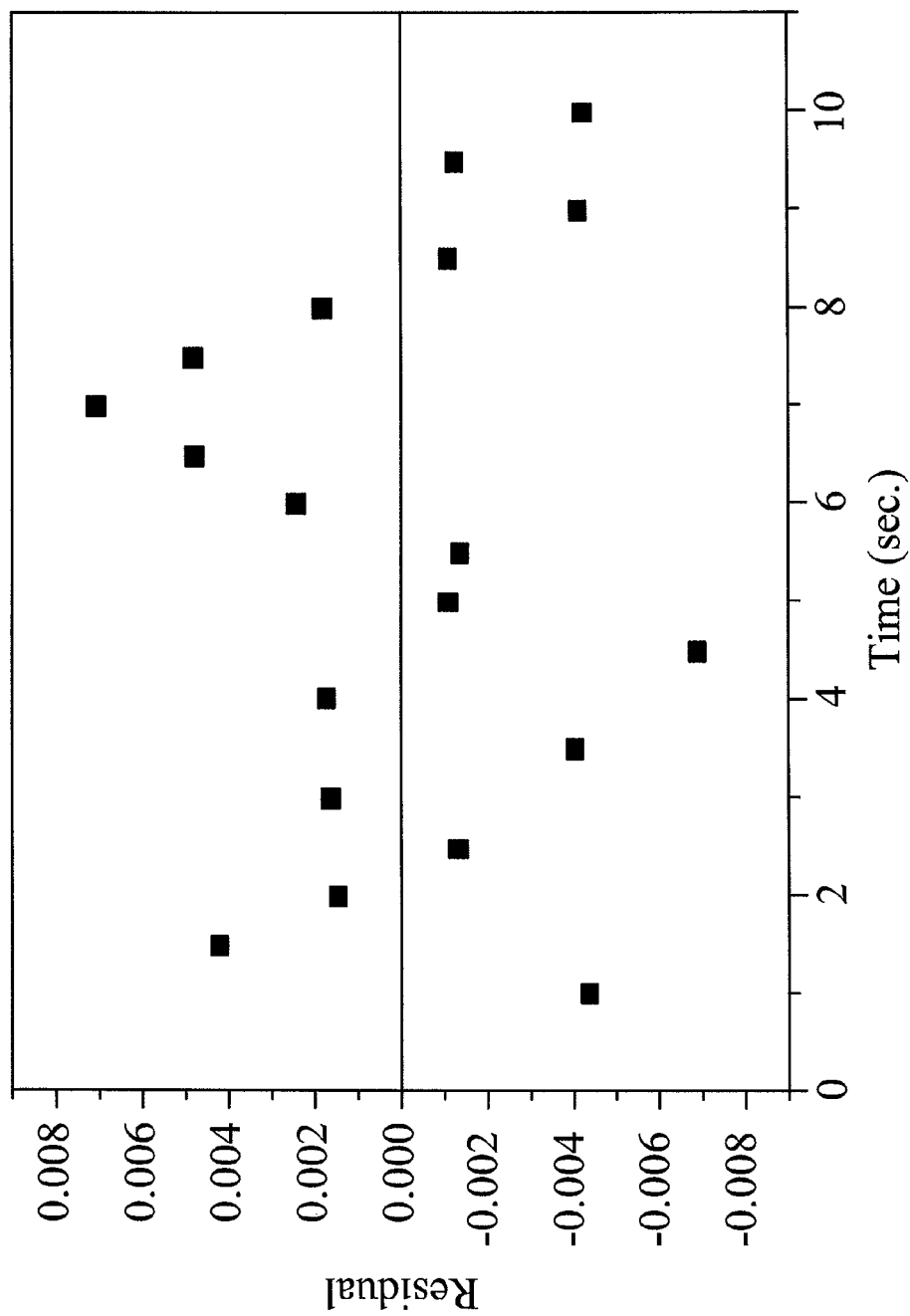
FIG. 7B is a diagram showing the residual analysis of the sample points and the linear regression line in FIG. 6B according to the first embodiment of the present invention.

Referring to FIG. 7A and FIG. 7B, FIG. 7A and FIG. 7B are diagrams showing the residual analysis of the sample points and the linear regression lines in FIG. 6A and FIG. 6B according to the first embodiment of the present invention. These two figures show that the sample points of the present invention have excellent agreement with the linear regression model.

Referring to Table 1 below, Table 1 is the association rate constant $k_a$ and the dissociation rate constant $k_d$ of anti-ovalbumin (anti-OVA) and ovalumin (OVA) binding system measured with the kinetic parameter estimation method of the present invention and various methods proposed by other reference documents. It can be realized in this Table that the present invention is able to estimate the association rate constant $k_a$ and the dissociation rate constant $k_d$ of the anti-ovalbumin (anti-OVA) and ovalumin (OVA) binding system.

TABLE 1

The association rate constant $k_a$ and the dissociation rate constant $k_d$ of the anti-ovalbumin (anti-OVA) and ovalumin (OVA) binding system measured with the kinetic parameter estimation of the present invention and various methods proposed by other reference documents.

| $k_a(M^{-1}s^{-1})$ | $k_d(s^{-1})$ | $K_f(M^{-1})$ | Reference |
|---|---|---|---|
| $(7.21 \pm 0.4) \times 10^3$ | $(2.97 \pm 0.1) \times 10^{-3}$ | $(2.43 \pm 0.2) \times 10^6$ | This study |
| $6.50 \times 10^5$ | $2.10 \times 10^{-3}$ | $3.10 \times 10^7$ | *Reference 1 |
| $1.06 \times 10^5$ | $2.49 \times 10^{-4}$ | $4.27 \times 10^8$ | **Reference 2 |

*Ref. 1: Masayuki Oda, Susumu Uchiyama, Carol V. Robinson, Kiichi Fukui, Yuji Kobayashi, and Takachika Azuma, *FEBS Journal* 2006, 273, 1476.
**Ref. 2: Kathryn L. Brogan, Jae Ho Shin, and Mark H. Schoenfisch, *Langmuir* 2004, 20, 9729.

Figure 8:
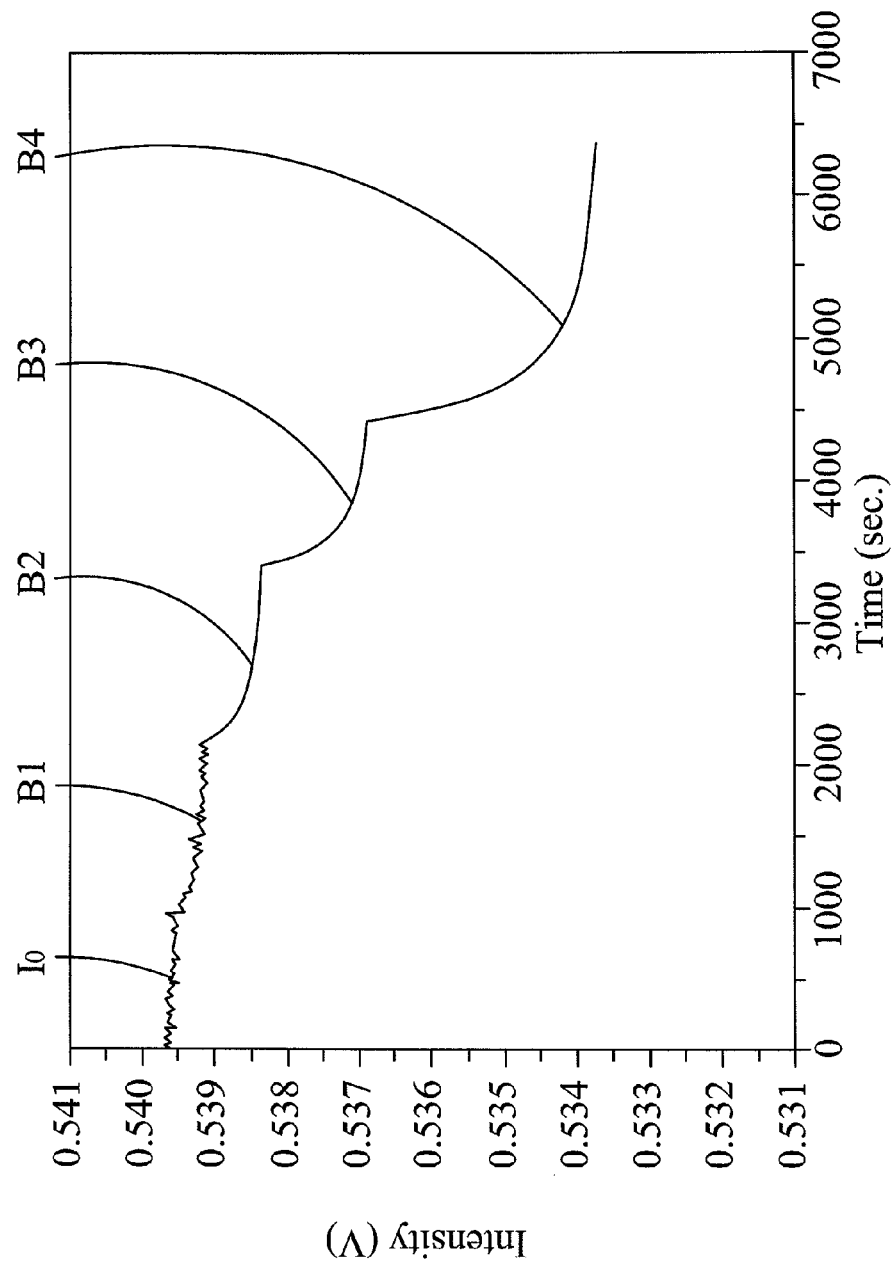
FIG. 8 is the curve diagram showing the use of mouse immunoglobulin (mouse IgG) as a bio-recognition layer and anti-mouse immunoglobulin (anti-mouse IgG) as a test solution according to a kinetic constant estimation method according to the second embodiment of the present invention.

Referring to FIG. 8, FIG. 8 is the curve diagram showing the use of mouse immunoglobulin (mouse IgG) as a bio-recognition layer and anti-mouse immunoglobulin (anti-mouse IgG) as a test solution with four different concentrations according to a kinetic constant estimation method described in the second embodiment of the present invention. The curve in the curve diagram comprises a first segment B1, a second segment B2, a third segment B3, and a fourth segment B4, wherein the third segment B3 and the fourth segment B4 represent the same test solution with two different concentrations. Obtain the time-resolved time-revolved light signal intensity values $I_1$ and $I_2$ starting at the initial reaction time of the first and the second segments in the curve diagram, the light signal intensity values $I_{eq1}$ and $I_{eq2}$ corresponding to the steady states of the first and the second segments, and the reference light signal intensity $I_0$, respectively. The concentrations of the anti-mouse immunoglobulin (anti-mouse IgG) test solutions in the first segment B1, the second segment B2, the third segment B3, and the fourth segment B4 are 1.3 nM, 5.2 nM, 10.4 nM, and 20.8 nM. The correlation coefficient of the data points sampling from the curve of FIG. 8 is 0.97.

Referring to Table 2 below, Table 2 is the association rate constant $k_a$ and the dissociation rate constant $k_d$ of mouse immunoglobulin (mouse IgG) and anti-mouse immunoglobulin (anti-mouse IgG) binding system measured with the kinetic parameter estimation method of the present invention and various methods proposed by other reference documents. It can be realized in this Table that the present invention is able to estimate the association rate constant $k_a$ and the dissociation rate constant $k_d$ of the mouse immunoglobulin (mouse IgG) and anti-mouse immunoglobulin (anti-mouse IgG) binding system.

TABLE 2

The association rate constant $k_a$ and the dissociation rate constant $k_d$ of the mouse immunoglobulin (mouse IgG) and anti-mouse immunoglobulin (anti-mouse IgG) binding system measured with the kinetic parameter estimation of the present invention and various methods proposed by other reference documents.

| $k_a(M^{-1}s^{-1})$ | $k_d(s^{-1})$ | $K_f(M^{-1})$ | Reference |
|---|---|---|---|
| $(1.45 \pm 0.2) \times 10^6$ | $(2.97 \pm 0.6) \times 10^{-2}$ | $(2.43 \pm 0.2) \times 10^7$ | This study |
| $5.25 \times 10^6$ | $8.00 \times 10^{-2}$ | $6.70 \times 10^7$ | *Reference 3 |
| $1.30 \times 10^6$ | $2.00 \times 10^{-4}$ | $6.70 \times 10^9$ | **Reference 4 |

*Ref. 3: L. Varghese, R. Sinha, J. Irudayaraj, *Anal Chim Acta* 2008, 625, 103.
**Ref. 4: D. Ivnitski, T. Wolf, B. Solomon, G. Fleminger, J. Rishpon, *Bioelectrochem. Bioenergetics* 1998, 45, 27.

Figure 9:
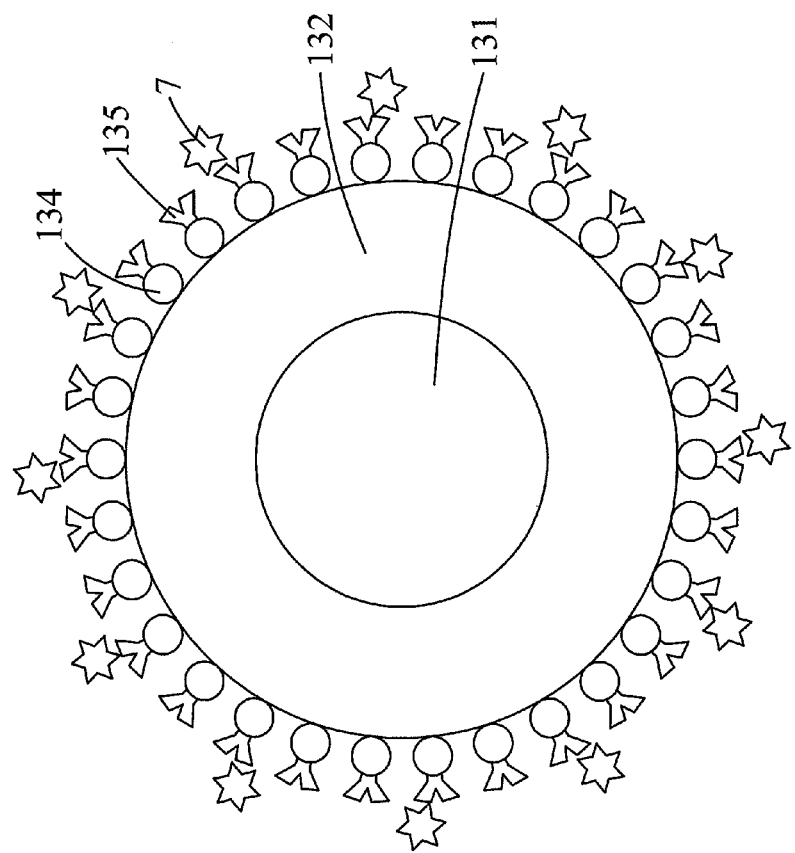
FIG. 9 is a diagram showing the binding reaction of the test solution and the bio-recognition layer according to the preferred embodiment of the present invention.

Referring FIG. 9, FIG. 9 is a diagram showing the binding reaction of the test solution and the bio-recognition layer according to the preferred embodiment of the present invention. It is noteworthy to mention when the test samples 7 in the test solution are binding with the bio-recognition layer 135, the nanoparticle layer 134 will generate the particle plasmon resonance due to the binding reaction. The particle plasmon resonance further changes the time-revolved light signal intensity. Thus, the estimation of the kinetic constants can be conducted by merely detecting the variation of time-revolved light signal intensity values.

It is noteworthy to further mention that the nanoparticle layer 134 will generate characteristic extinction spectrum as it is excited by a light beam, and this characteristic spectrum is called particle plasmon resonance (PPR) spectrum. The basic detection principle of the particle plasmon resonance sensing system is as follows: when the refractive index of the surrounding environment of the nanoparticle layer changes, the peak wavelength and the extinction cross-section of the particle plasmon resonance spectrum will change accordingly. In the waveguide aspect, a light beam with a specific frequency will interact with the nanoparticle layer to generate the particle plasmon resonance (PPR) at every reflection interface. The higher number of reflections, the more energy loss from the multiple total internal reflections at the interface, thus decreases the emergent light intensity of the fiber. To sum up, the effect of the particle plasmon resonance can be accumulated by the multiple total internal reflections, thus achieves the goal of enhancing the sensor sensitivity.

It is noteworthy to further mention that the injections of the first test solution and the second test solution stop as the first tube is filled up, then each test solution stay in a static state, respectively. The time duration for a test solution to fill up the first tube should be far less than the time consumption for the test solute to bind with the probe molecules on the bio-recognition layer after diffusion. The decision of the injection time of a test solution references to the following criteria: the injection time should be less than one half of that of as the received light intensity enables the fraction $[(I_t-I_{eq})/(I_0-I_{eq})]$ to reach 0.4, wherein $I_0$ and $I_{eq}$ are the light signal intensity values of the reference test solution and of steady state equilibrium, respectively. Contrarily, the time duration of the time-revolved light signal intensity, as the test solution is injected yet not in a steady state or the ratio $[(I_t-I_{eq})/(I_0-I_{eq})]$ is already greater than 0.4, will be adopted. Under the assumption of the pseudo-first order reaction rate equation, the variation of the complex concentration versus time is equal to the binding rate of the test solute with the probe molecules of the bio-recognition layer minus the variation of the complex concentration versus time. When the complex concentration is proportional to the time-revolved light signal intensity, it is derived that the logarithm of $[(I_t-I_{eq})/(I_0-I_{eq})]$ presents a linear relationship with time. In FIG. 6A the last selected signal values for the first segment B1 and the second segment B2 are substituted into $[(I_t-I_{eq})/(I_0-I_{eq})]$ to calculate the ratios, respectively. The two ratios are both 0.1, less than the aforementioned reference value 0.4.

In summary, the method for obtaining binding kinetic rate constants using a fiber optic particle plasmon resonance (FOPPR) sensor of the present invention comprises at least the following advantages:

the method for obtaining binding kinetic rate constants using a fiber optic particle plasmon resonance (FOPPR) sensor of the present invention utilize N different test solutions to obtain a curve diagram of time-revolved light signal intensity of the N concentrations. N slopes can be obtained after a linear regression over the above curve diagram. After executing another linear regression over the N slopes versus the N concentrations, finally the $k_a$ value and the $k_d$ value can be obtained, wherein the N value is equal to or greater than 2.

The present invention does not need to use a fluorescent mechanism to mark the test analyte, thus it will not influence the characteristics of the test analyte. Moreover, the present invention detects the time-revolved light signal intensity after the test solution is quickly injected and remains in static mode. Unlike the conventional plasmon resonance sensor (for example, the Biacore system), the estimation of the association constant $k_a$ and the dissociation constant $k_d$ by the present invention does not need to consider the injection rate of the test solution.

In summary, although the present invention has been described with reference to the foregoing preferred embodiment, it will be understood that the invention is not limited to the details thereof. Various equivalent variations and modifications may still occur to those skilled in this art in view of the teachings of the present invention. Thus, all such variations and equivalent modifications are also embraced within the scope of the invention as defined in the appended claims.

What is claimed is:

1. A method for obtaining the binding kinetic rate constants using a fiber optic particle plasmon resonance (FOPPR) sensor, comprising the steps of:
   providing a fiber optic particle plasmon resonance sensor, wherein the fiber optic particle plasmon resonance sensor at least comprises:
   a light source to emit a light beam;
   a photoreceiver; and
   a fiber sensor chip, wherein the fiber sensor chip is located between the light source and the photoreceiver and the fiber sensor chip comprises:
   an optical fiber, wherein the optical fiber comprises a first region and a second region; the first region is located at two corresponding sides of the second region, wherein the first region comprises a fiber core, a cladding, and a protective layer, the refractive index of the fiber core is greater than that of the cladding such that the light beam can propagate within the fiber core; and the second region comprises the fiber core, the cladding, a noble metal nanoparticle layer, and a bio-recognition layer;

a first plate, wherein the first plate comprise a trench and the trench is used to place the optical fiber; and a second plate, wherein a first tube and second tube are vertically installed on one side of the second plate, the first tube is hollow and comprises a first opening, the second tube is hollow and comprises a second opening, the first tube and the second tube are connected to the second plate, the other side of the second plate which is opposite to the first plate is face-to-face against the side of the first plate containing the trench such that the optical fiber can be placed between the first plate and the second plate and into the trench within the first plate, and the second plate is placed face-to-face against the first plate to seal them off;

allowing the light beam from the light source of the fiber optic particle plasmon resonance sensor to enter the fiber sensor chip and propagate within the fiber core due to total internal reflection, and let the photoreceiver of the fiber optic particle plasmon resonance sensor receive a light signal;

quickly injecting a reference solution into the first opening of the first tube, wherein the first opening serves as a flow inlet;

injecting N test solutions sequentially into the first opening of the first tube, such that each of the test solutions quickly flows onto the bio-recognition layer of the fiber sensor chip and remains in a static condition within the trench till the next injection, wherein each of the test solutions comprises a separate concentration $C_i$, where an integer i is from 1 to N, and the number of N is equal to or greater than 2;

converting, with the fiber optic particle plasmon resonance sensor, the light signals received by the photoreceiver into a time-resolved curve diagram of time-revolved light signal intensity, wherein the number of segments i in the curve of the curve diagram is the same as that of test solutions of concentration $C_i$, and each segment numbered as i is corresponding to the time-resolved light signal intensity generated by each of the injected test solutions of concentration C, in sequence, respectively;

obtaining each of the time-resolved light signal profiles starting at the initial time of the segments in the curve diagram $I_t$, the time-revolved light signal intensity values of the segments at the steady states $I_{eq}$, and the reference light signal intensity $I_0$ corresponding to the average signal intensity level of the reference solution;

obtaining the time-revolved light signal intensity values $I_t$ at the initial time when each of the test solutions has filled up the trench and remains at a static condition, taking $I_t$ into a formula $[(I_t-I_{eq})/(I_0-I_{eq})]$ to calculate a plurality of logarithm values of the fraction formula, $\ln[(I_t-I_{eq})/(I_0-I_{eq})]$, when the reference light signal intensity prior to the initial time is not obtained using the reference solution (i.gtoreq.2), subtracting each logarithm value by $\ln[(I_0-I_{eqi})/(I_{eqi(i-1)}-I_{eqi})]$ to adjust the intercept of the linear formula as zero, and executing a linear regression by using the logarithm values versus time to obtain a plurality of linear line diagrams corresponding to the number of the segments;

obtaining a slope $S_i$ of a linear line in the plurality of linear line diagrams; and using the concentrations $C_i$ and the corresponding slopes $S_i$ to execute another linear regression to obtain a slope and an intercept of each regression line, then taking the results into a concentration-versus-slope linear equation $S(C_i)=k_a C_i + k_d$ to obtain an association constant $k_a$ and a dissociation constant $k_d$.

2. The method for obtaining the binding kinetic rate constants using a fiber optic particle plasmon resonance sensor of claim 1, wherein the first plate or the second plate is made of plastic.

3. The method for obtaining the binding kinetic rate constants using a fiber optic particle plasmon resonance (FOPPR) sensor of claim 1, wherein the fiber core is made of silicon oxide and the cladding is made of polymeric material.

4. The method for obtaining the binding kinetic rate constants using a fiber optic particle plasmon resonance (FOPPR) sensor of claim 1, wherein the bio-recognition layer comprises a bio-molecule.

5. The method for obtaining the binding kinetic rate constants using a fiber optic particle plasmon resonance (FOPPR) sensor of claim 1, wherein the noble metal nanoparticle layer is made of gold.

6. The method for obtaining the binding kinetic rate constants using a fiber optic particle plasmon resonance (FOPPR) sensor of claim 1, wherein the noble metal nanoparticle layer comprises a plurality of gold nanospheres.

7. The method for obtaining the binding kinetic rate constants using a fiber optic particle plasmon resonance (FOPPR) sensor of claim 1, wherein the fiber optic particle plasmon resonance sensor further comprises:
 a power supply unit for generating a functional driving signal of a fixed frequency and a fixed voltage to drive the light source to generate the light signal;
 a signal processing unit for receiving a reference signal generated by the power supply unit, and the signal processing unit receives the light signal coming from the photoreceiver and correlates the light signal with the reference signal to generate a processed signal; and
 a computer for receiving the processed signal coming from the signal processing unit to save as a data file and displays the data file for evaluation.

8. The method for obtaining the binding kinetic rate constants using a fiber optic particle plasmon resonance (FOPPR) sensor of claim 1, wherein the concentrations of the test solutions to inject into the first tube are increasing in accordance with an order of injection.

9. The method for obtaining the binding kinetic rate constants using a fiber optic particle plasmon resonance (FOPPR) sensor of claim 7, wherein the power supply unit is a waveform generator and the signal processing unit is a lock-in amplifier.

* * * * *